(12) United States Patent
Gordon

(10) Patent No.: US 7,387,898 B1
(45) Date of Patent: Jun. 17, 2008

(54) APPARATUS AND METHOD FOR CONDUCTING ASSAYS

(75) Inventor: John Francis Gordon, Glasgow (GB)

(73) Assignees: Burstein Technologies, Inc., Irvine, CA (US); Nagaoka & Co., Ltd., Hyogo (JP)

( * ) Notice: Subject to any disclaimer, the term of this patent is extended or adjusted under 35 U.S.C. 154(b) by 0 days.

(21) Appl. No.: 09/284,421

(22) PCT Filed: Oct. 8, 1997

(86) PCT No.: PCT/GB97/02708

§ 371 (c)(1),
(2), (4) Date: Jun. 11, 1999

(87) PCT Pub. No.: WO98/15356

PCT Pub. Date: Apr. 16, 1998

(30) Foreign Application Priority Data

Aug. 10, 1996 (GB) .................................. 9620934.1

(51) Int. Cl.
*G01N 21/05* (2006.01)
*G01N 21/07* (2006.01)

(52) U.S. Cl. .......................... 436/165; 436/45; 436/164; 436/180; 422/58; 422/64; 422/68.1; 422/82.05; 422/100; 422/102; 435/287.3; 435/288.3; 435/288.7

(58) Field of Classification Search .................. 422/55, 422/57, 58, 64, 68.1, 82.05, 82.07, 102, 104; 435/287.2, 287.3, 287.9, 288.3, 288.9, 288.7; 436/518, 45, 46, 49, 164–166, 172, 177, 436/180

See application file for complete search history.

(56) References Cited

U.S. PATENT DOCUMENTS

| 4,483,925 A | * | 11/1984 | Noack .......................... 435/293 |
| 4,596,695 A |   | 6/1986  | Cottingham .................. 422/58 |
| 4,722,598 A | * | 2/1988  | Ford ............................ 356/246 |
| 4,900,513 A | * | 2/1990  | Barker et al. .................. 422/64 |
| 4,961,906 A | * | 10/1990 | Andersen et al. ............ 422/102 |

(Continued)

FOREIGN PATENT DOCUMENTS

EP          417305 A1  *   3/1991

(Continued)

*Primary Examiner*—Maureen M. Wallenhorst
(74) *Attorney, Agent, or Firm*—Knobbe Martens Olson & Bear LLP

(57) ABSTRACT

A multi-well assay plate structure (54) and assay apparatus and a method for performing chemical biochemical assays is described. The multi-well assay plate structure (54) defines a relatively shallow substantially enclosed space (71) above a plurality of wells (76), with the enclosed space (71) having an inlet (72) and an outlet (22) separate from the inlet. Fluid introduced via the inlet (72) flows into the space (71) and/or wells (76) by displacing air. Withdrawal of the fluid via the inlet (72) or outlet leaves fluid in the wells (76) allowing various tests to be performed. Various embodiments of the structure are described. The preferred arrangement embodies the structure on a transparent plastic disk which can be used with automatic fluid handling apparatus (80) and the results assessed using optical assessment apparatus (81). The apparatus can be used to perform a variety of assays but, in particular, biochemical/chemical assay, immunoassays and genetic (DNA) assays and it can be used in a laboratory for multiple sample testing or at a point-of-care, i.e. in a surgery or clinic.

39 Claims, 5 Drawing Sheets

U.S. PATENT DOCUMENTS

| | | | |
|---|---|---|---|
| 5,041,266 A | * | 8/1991 | Fox .............................. 422/102 |
| 5,167,922 A | * | 12/1992 | Long ............................ 422/58 |
| 5,310,523 A | * | 5/1994 | Smethers et al. .............. 422/57 |
| 5,496,520 A | * | 3/1996 | Kelton et al. .................. 422/64 |
| 5,545,540 A | | 8/1996 | Mian ........................ 435/91.2 |
| 5,585,069 A | * | 12/1996 | Zanzucchi et al. ........... 204/450 |
| 5,700,655 A | * | 12/1997 | Croteau et al. ................ 435/30 |
| 5,792,654 A | * | 8/1998 | Bohannon et al. ........ 435/305.3 |
| 5,955,352 A | * | 9/1999 | Inoue et al. .............. 435/287.7 |
| 6,027,695 A | * | 2/2000 | Oldenburg et al. ........... 422/102 |
| 6,027,873 A | * | 2/2000 | Schellenberger et al. ........ 435/4 |
| 6,143,496 A | * | 11/2000 | Brown et al. .................. 422/58 |
| 6,268,209 B1 | * | 7/2001 | Pierson et al. .............. 422/100 |

FOREIGN PATENT DOCUMENTS

| | | | |
|---|---|---|---|
| EP | 0435246 A2 | | 3/1991 |
| GB | 2147100 A | | 5/1985 |
| GB | 1 557 984 | | 12/1999 |
| WO | WO94/29484 | | 12/1994 |
| WO | WO95/25815 | | 9/1995 |
| WO | 96/09548 | * | 3/1996 |
| WO | WO96/17959 | | 6/1996 |
| WO | WO97/21090 | | 6/1997 |

* cited by examiner

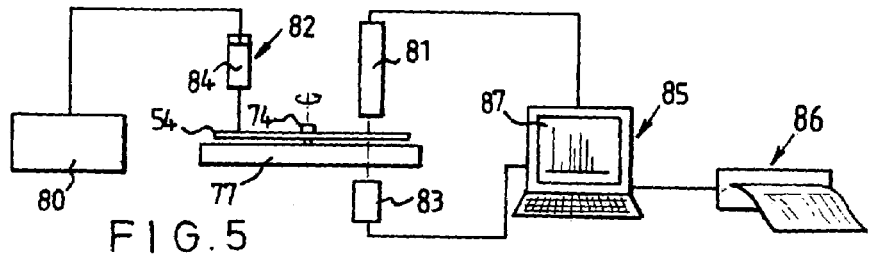
FIG. 5
| Data | Clear plastic | Clear plastic +Blue reaction agent +Blocking agent | Seven antigen assay | | | | | | |
|---|---|---|---|---|---|---|---|---|---|
| | 76.4 | 80.2 | 106.6 | 108.8 | 103.3 | 103.4 | 102.2 | 103.6 | 108.8 |
| | 76.4 | 85.5 | 106.4 | 103.9 | 101.3 | 102.7 | 98.5 | 111.2 | 109 |
| | 76.83 | 81.4 | 105.4 | 103.1 | 105.2 | 104.2 | 101 | 106.2 | 109.5 |
| | 74.53 | 81.6 | 106.5 | 104.7 | 104.7 | 106.4 | 100.7 | 102.9 | 106.4 |
| | 78.62 | 82.6 | | | | | | | |
| | 76.75 | 79.6 | | | | | | | |
| | 77.6 | 78.9 | | | | | | | |
| | 77.8 | 83.3 | | | | | | | |
| Mean-bkgd | | 5 | 29.4 | 28.3 | 26.9 | 27.4 | 23.8 | 29.2 | 31.6 |
| St.Dev | 0.56 | 2.44 | 0.56 | 2.44 | 1.75 | 1.60 | 1.54 | 3.76 | 1.38 |
FIG. 6a
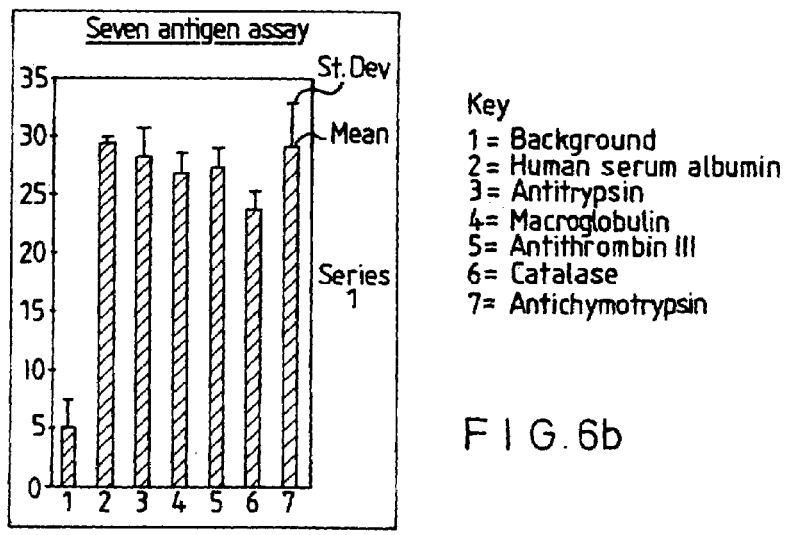
Key
1 = Background
2 = Human serum albumin
3 = Antitrypsin
4 = Macroglobulin
5 = Antithrombin III
6 = Catalase
7 = Antichymotrypsin
FIG. 6b

APPARATUS AND METHOD FOR CONDUCTING ASSAYS

STATEMENT REGARDING FEDERALLY SPONSORED RESEARCH OR DEVELOPMENT (Not Applicable).

CROSS-REFERENCES TO RELATED APPLICATIONS

This application is a Section 371 application based upon PCT/GB97/02708 filed Oct. 8, 1997, and United Kingdom application 9620934.1, filed Aug. 10, 1996.

BACKGROUND OF THE INVENTION

1. Field of the Invention

The present invention relates to apparatus and to a method for conducting assays and, in particular, to multi-well plate structures for receiving and holding, in separate wells, volumes of liquid for the purpose of conducting chemical or biochemical assays. Multi-well trays or plates having a 2-dimensional array of small wells are commonly used in medicine and science to facilitate testing of a liquid analyte. One particular area of use is blood screening where blood or blood products are introduced into the wells to test for viruses such as HIV, heptitis etc.

2. Description of the Related Art

Such tests (immunoassays) typically involve an antigen-antibody interaction, where the surfaces of the wells are coated with specific antigen itself. This approach detects circulating antibodies to that specific antigen. Alternatively the wells can be coated with a specific antibody which captures circulating antigen which is, in turn, identified by a second antibody directed against a second epitope on the captured antigen. These two approaches are just two of the large number of variants developed in immunoassay (review Principles and Practice of Immunoassay Price & Newman 1997 ISBN 1-56159-145-0).

In an immunoassays sample must be applied and in most cases subsequent addition of reagents or washing buffer is required. Typically the well is exposed to blood or blood product and the well is rinsed clean and a further reactant, which binds either to exposed antibodies or captured antigens is introduced into the wells, to create an observable reaction. These reactions may produce a colour or some other observable change. This enables the wells containing specific antigen antibody reactions to be identified and the extent of these reactions quantified.

It is often necessary to fill each well of a multi-well tray with a precisely defined volume of analyte. This is normally achieved using a single or multi-headed micro-pipette. However, this process is often time consuming and, particularly where a large number of wells are to be filled can lead to a number of wells being missed.

BRIEF SUMMARY OF THE INVENTION

In certain circumstances it is necessary that the wells of a tray be contained within a substantially closed container, e.g. to avoid the risk of contamination of the wells and of leakage of contaminated material. With trays such as this, it may be difficult or impossible to gain access to the wells to enable them to be filled using a micro-pipette.

It is an object of the present invention to overcome or at least mitigate the disadvantages of known multi-well trays.

This is achieved by providing a multi-well assay plate structure which defines a relatively shallow substantially enclosed space above a plurality of wells, with the enclosed space having an inlet and an outlet separate from the inlet. Fluid introduced via the inlet flows into the space, and covers the wells, by displacing air. Withdrawal of the fluid from the space via the inlet or outlet leaves fluid in the wells allowing various tests to be performed.

According to a first aspect of the present invention there is defined a multi-well assay plate structure comprising:
a first upper surface,
a second lower surface having a plurality of wells disposed therein,
the first and second surfaces defining a chamber having an inlet and an outlet, the inlet and outlet allowing fluid to be introduced and withdrawn from the chamber, the wells being proportioned and dimensioned to retain a volume of fluid in each well following withdrawal of the liquid.

Preferably, the chamber is shallow enough to allow fluid to fill the wells and the chamber. The wells are deep enough to retain a volume of fluid following withdrawal of fluid in the space above the wells.

The plate structure can be of any convenient shape but, advantageously, is sector-shaped with a detachable handle at the longer arc-portion to facilitate locating the sector on a disc. Conveniently, a plurality of sector-shaped structures are located on the disc.

Conveniently, also the sectors and discs are made of plastic and the sectors can be snap-fitted onto the disc. The sectors and the disc include lock and key portions to allow the sectors to be snap-fitted in the correct orientation only.

Alternatively, a disc with a plurality of separate sections can be manufactured or moulded in one piece instead of snap-in sectors.

The composite structure may be snap-fitted onto a compact disk.

The disk structure may have a circumferential gutter extending around its periphery to facilitate collection of fluid following fluid introduction/withdrawal from the chamber.

The wells are dimensioned and proportioned in terms of diameter and depth to receive and retain fluid containing the analyte or part of the reagent under test. The exact dimensions are a matter of choice and depend on a number of parameters such as the type of material of the surfaces of the chamber and wells; viscosity of the fluid and the depth (height) of the space between the first and second surfaces.

Advantageously, the dimensions of the structure are such that the wells fill to retain sufficient fluid the space is flooded and withdrawal to allow a measurable reaction to be measured within an individual well without contribution from adjacent wells. The overall process of sequential steps of flood and fill is advantageous in that it allows both discrete measurements within individual wells when filled and efficient washing of an array of wells (flood) which is useful in multistep procedures, such as immunoassays, which requires sequential application of reagents interspersed with rigorous washing steps. This permits the wells to be cleaned or rinsed in the same way as filling to allow subsequent tests to be carried out within an individual well whilst avoiding cross-contamination between adjacent wells.

The structure is preferably made of transparent or otherwise optically transmissive plastic to facilitate optical reading of the wells to determine the results of the tests. Conveniently, the structure is integrated with automatic fluid handling apparatus and an optical reader of allow automatic fluid handling and optical assessment of the results of the reactions. Alternatively, fluid handling can be manually controlled and the results of the reactions within the structure can be assessed by an optical reader or be scored by visual assessment.

According to a second aspect of the present invention there is provided a multi-well assay structure comprising an upper surface and a lower closely spaced opposed surface, said upper and lower surfaces defining a relatively shallow space therebetween, the lower surface having a plurality of wells therein, at least two spaced apart openings providing access to said space from an external location, wherein a fluid introduced into said space through one of said openings fills substantially all of the space and covers of the wells and said fluid, when subsequently withdrawn through the same or the other opening, leaves the wells filled with liquid.

The volume of fluid introduced into each well when using the structure of the present invention is substantially defined by the volume of the well. The accuracy and precision with which the wells can be filled is therefore defined by the accuracy and precision with which the wells can be fabricated and which is generally high. Furthermore, the multiplicity of wells can be filled by way of a single injection and withdrawal of fluid through an opening into the space containing the wells, so that the wells can be filled extremely rapidly.

The structure of the present invention provides for the filling of a plurality of wells in a substantially closed chamber, the only openings into that container being the fluid injection opening and a second 'vent' opening.

The structure of the present invention simplifies the process of cleaning or rinsing previously filled wells as this can be achieved by repeatedly injecting and withdrawing fluid through one of said openings.

Conveniently, the spacing between said upper and lower surfaces is sufficiently small to facilitate the flow of fluid in said space by capillary or capillary like action. Typically, the spacing is less than 1 mm and preferably less than 0.5 mm.

Preferably, said upper and lower surfaces are substantially planer.

The wells may have any suitable geometry. For example, the wells may be provided in said lower surface by blind circular holes with a semi-spherical termination. Alternatively, the wells may have substantially straight sidewalls, e.g. so that the sidewalls extend substantially vertically and terminate in a flat base. Vertical sidewalls assist in preventing the transfer of fluid between adjacent wells.

The surfaces may be provided by respective upper and lower plates which are spaced apart by one or more spacer walls.

Preferably, the opening through which fluid is introduced into said space is provided through either the upper or lower surface and, more preferably, through the upper surface. The additional opening may be provided through said upper or lower surface or through a side surface.

Preferably, said opening for introducing a fluid comprises a relatively small opening arranged to receive the end of a syringe or similar liquid injecting device, where the opening forms a substantially air-tight seal around said end.

Preferably, said lower surface of the container is treated to increase the hydrophobicity to facilitate smooth flow of liquid across the sector and hydrophilicity to aid movement of liquid into desired locations, e.g. wells. This helps to prevent the formation of air pockets in the space and aids filling of the wells. The treatment may comprise for example exposing the surface to a wetting agent, e.g. poly-1-lysine, or exposing the surface to a gas plasma.

In one embodiment of the present invention, the multi-well structure is embodied in a disc. The disc effectively comprises upper and lower circular plates, the internal surfaces of which respectively define said upper and lower opposed surfaces. Preferably, said opening for introducing liquid into the space is a hole passing through the upper circular plate. Preferably, the second opening is provided at the peripheral edge of the disc. The space between the upper and lower plates is subdivided, by one or more dividing walls, to provide a plurality of multi-well plates in which case each space is provided with an opening and a vent to enable each space to be independently filled. The dividing walls may extend radially and/or may be concentric to one another.

Preferably, at least one of the upper and lower plates forming the container are transparent to enable optical inspection of the wells from outside the container. The other of the upper and lower plates may comprise a reflecting surface so that radiation entering into the container through the transparent plate transverses the container in both directions, resulting in an improved signal detection for optical inspection.

In an alterative embodiment of the present invention there is provided a disc arranged to receive a plurality of sector (pie) shaped inserts each of which comprises a generally planar upper surface having a plurality of wells provided therein. For each insert, the disc comprises a substantially planar surface arranged, in use, to oppose said substantially planar insert surface and means for retaining the insert in position so that the respective planar surfaces are in closely spaced opposition to one another, and said at least two openings.

Preferably, the opening for filling the container is provided through the planar surface of the disc. The vent opening is preferably provided at, or adjacent to, the peripheral edge of the disc.

The disc preferably comprises upper and lower circular plates separated by radially extending spacers. The spacers define slots between the plates for receiving said inserts. Preferably, said planar surface of each insert comprises upstanding walls around at least a portion of its periphery for the purpose of sealing the inner edges of the insert to the opposed planar surface of the disc, thereby to prevent seepage of liquid around the insert.

According to a third aspect of the present invention there is provided a method of filling the wells of the multi-well structure of the above first aspect of the present invention, said method comprising the steps of:

introducing a fluid into said chamber through one of said openings to substantially flood the chamber;

and subsequently withdrawing the fluid from the chamber through the same or the other opening to leave liquid in the wells.

Preferably, the method further includes the step of forming an air tight seal between the fluid inlet and an end region of a syringe or similar liquid injecting device, and injecting fluid through the opening into the chamber and subsequently sucking liquid out of the space through the opening.

According to a fourth aspect of the present invention there is provided a method of conducting a chemical or biochemical assay said method comprising the steps of:

providing a surface within a substantially enclosed chamber having a plurality of wells at spaced locations sufficient to allow a reaction at each well location, treating each well with a first reagent, flooding the enclosed chamber and covering the wells with a fluid carrying at least a second reagent, removing excess fluid from said chamber to leave a mixture of said first and second reagents in each well, and optically assessing each well and determining if a reaction occurred and correlating the reaction results to provide an assay of the chemical or biochemical reactions under test.

Preferably, the step of optical assessment is carried out automatically using optical reading apparatus.

Preferably also, the surfaces with the wells having first fluid carrying reagents are prior prepared for loading into the structure.

Conveniently, the fluid carrying at least the second reagent is introduced into the structure and withdrawn from the structure using suitable automatic fluid handling apparatus.

Conveniently also, after optical assessment of the results of the assay, the automated fluid handling apparatus is used to inject and withdraw rinsing fluid a predetermined number of times from the well tray to clean the wells for receiving subsequent samples for assay.

According to a fifth aspect of the present invention, there is provided chemical/biochemical assay apparatus comprising an assay plate structure defined in said first aspect and having a plurality of wells for receiving samples to be assayed, fluid handling means for introducing and removing fluid reagents into said assay plate structure to allow a fluid reagent mixture to be retained in each well, and optical assessment means for measuring optical result of the reaction in each well.

Preferably, the fluid handling means and the optical assessment means are automated.

According to a sixth aspect of the present invention there is provided an assay plate structure for use in conducting optical assays of a fluid analyte, the plate structure comprising:

a disc for rotation about a central axis, the disc having upper and lower plates and a plurality of substantially radially extending walls disposed between the plate, wherein said walls sub-divide the disc into a plurality of disc sectors; and a plurality of disc inserts arranged to be received by respective disk sectors and to be retained therein, the structure further having a plurality of openings through the upper surface, at least one opening above each disc sector for introducing a liquid analyte into the sector space between the plate and the disc insert.

Preferably, the disc further comprises a lower plate, spaced apart from said upper plate by said radially extending walls. More preferably, the upper and lower plates are circular.

Preferably, the upper surface of each disc insert and the opposed surface of the plate are substantially planar, and, more preferably, are in a closely spaced arrangement.

Preferably, a vent opening is provided for each disc segment around the periphery thereof, between the radially outer edge of the upper plate and each disc insert.

These and other aspects of the present invention will now be described with reference to the accompanying drawings, in which:

BRIEF DESCRIPTION OF THE SEVERAL VIEWS OF THE DRAWINGS

FIG. 5 depicts chemical/biochemical assay apparatus for conducting an assay on reactions carried out using the multi-well assay plate structures shown in FIG. 3 or FIGS. 4a, b, c and d, and FIGS. 6a and 6b depict the data and graphs respectively of antigen/antibody biochemical assays carried out using the apparatus of FIG. 5 on the assay plate shown in FIG. 4a, b, c and d.

DETAILED DESCRIPTION OF THE INVENTION

Figure 1:
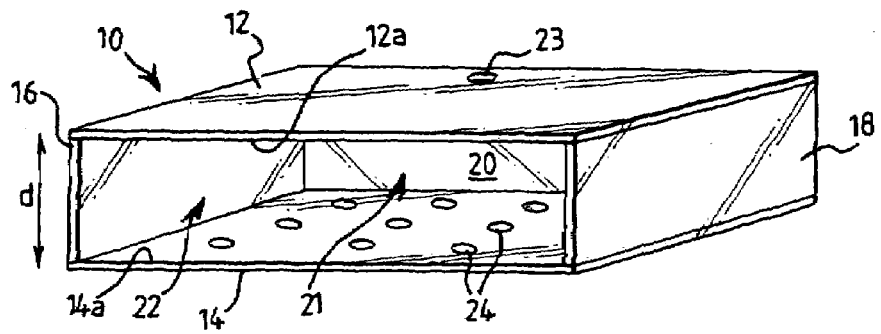
FIG. 1 is a diagrammatic representation of a multi-well assay plate structure according to a first embodiment of the present invention.

Reference is first made to FIG. 1 which shows a multi-well assay plate, generally indicated by reference numeral 10, having a box-like construction with a rectangular cross-section. The assay plate 10 comprises an upper plate 12, a lower plate 14, and side and rear spacers 16,18,20 all of which are made of a transparent polycarbonate. The front of the box, indicated generally by the reference numeral 22, is open to the surrounding space.

The spacers 16,18,20 are dimensioned to produce a space 21 of uniform spacing d between the opposed inner surfaces 12a,14a of the upper and lower plates 12,12. Spacing d is chosen such that a selected liquid is able to flow through the space 21 between the upper and lower plates 12,14 in a controlled manner by capillary or capillary-like action. Generally, d is less than 0.5 mm.

A small opening 23 extends through the upper plate 12 to communicate the inner space 21 with the exterior space surrounding the container. Opening 23 is located close to the rear wall 20 in order to prevent air-locks forming in the container during filling as will be described in more detail below.

A regular array of wells or depressions 24 are formed in the upper surface 14a of the lower plate 14. Typically, the polycarbonate assay plate with wells 24 is produced by suitably moulding the lower plate 14 or by etching or pressing. The wells 24 are 2 mm in diameter and 1 mm deep and typically have a volume of 5 μl and any suitable number of wells may be provided. The wells are spaced 4 mm apart (centre or centre).

Figure 2A:
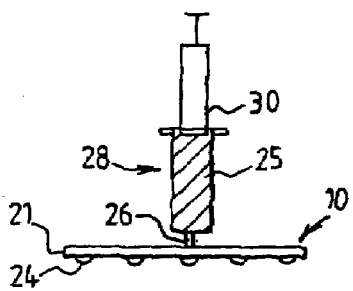
FIGS. 2a to 2c illustrate the steps involved in filling the wells of the container of FIG. 1.
Figure 2B:
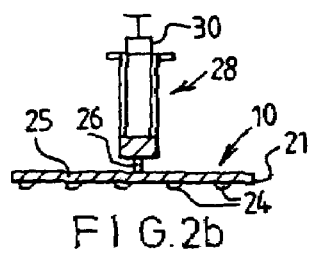
Figure 2C:
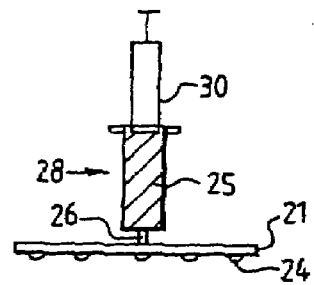
Figure 2D:
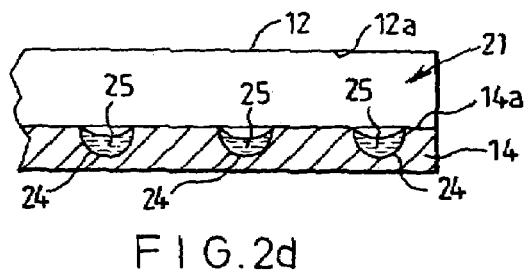
FIG. 2d is an enlarged detail of part of the structure of FIGS. 2a to 2c.

FIGS. 2a to 2c illustrate the process by which the wells 24 of the assay plate 10 are filled with a liquid analyte 25. The end 26 of a syringe 28 containing the liquid analyte 25 is pressed into the opening 23 provided in the upper plate 12 of the container 10 (FIG. 2a) so as to form an air-tight seal between the periphery of the syringe and the inner surface of the opening 23. The plunger 30 of the syringe 28 is then depressed to force the liquid 25 through the opening 23 into the space 21 within the plate 10. As best seen in FIG. 2b, due to the capillary or capillary like flow of liquid through the space 21, the entire space 21 is filled and wells 24 are covered before liquid 25 beings to flow through the front open face 22 of the container 10. When it is observed that all of the space 21 is filled and the wells 24 are covered with liquid, and preferably prior to liquid flowing out through the front face 22, the plunger 30 of the syringe 28 is withdrawn. This action empties the space 21 of liquid, but results in the wells 24 being filled with liquid 25 as shown in FIG. 2c. FIG. 2d shows an enlarged cross-sectional view through part of the assay plate structure and showing how liquid is retained in wells 24 up to the meniscus. As with the filling process, liquid flows from the space 21 in a controlled manner. No puddles or drops of liquid remain in the space 21, other than in the wells 24.

It will be appreciated that prior to introducing the liquid analyte 25 into the space 21, for example during the manufacture of the assay plate 10, the wells 24 of the plate 10 may be coated with an appropriate reactant. For example, if it is desired to conduct antigen-antibody reactions, the wells 24 are coated with an antigen. The remainder of the surface 14a is coated with a blocking agent to prevent antigen and antibodies from binding to surface 14a. Once the wells 24 have been filled with the liquid analyte 25, any antibodies present in the liquid analyte 25 will bind with the antigens contained in the wells 24. There is no binding of the antibodies to surface 14a. If it is necessary to conduct a further reaction in the wells 24, e.g. to bind a coloured or fluorescent label to the bound antibodies or exposed antigens, it is possible to repeat the steps of FIGS. 2a to 2c in order to introduce the labelled components into the wells 24. Prior to introducing the labelled components, if it is necessary to rinse the wells 24 and the inner surfaces 12a,14a of the plate 10, this is again easily achieved by repeating steps 2a to 2c with the syringe 28 containing, for example, distilled water.

Figure 3:
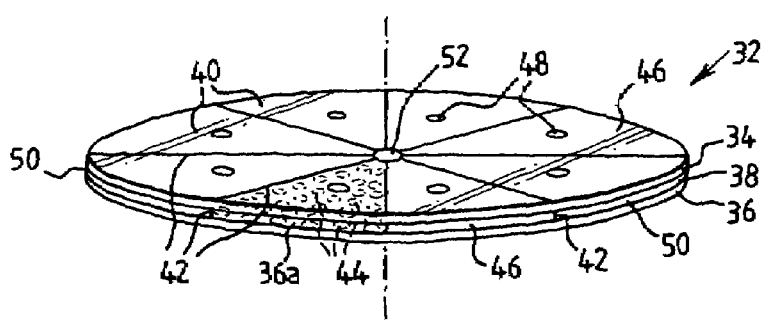
FIG. 3 shows a multi-well assay plate structure according to a second embodiment of the present invention.

There is illustrated in FIG. 3 a second embodiment of the present invention which depicts a multi-well assay plate in the form of a disk 32 designed for use with a rotating scanning device having a CD player type format. One such device is described for example in WO96/09548. The disk 32 shown in FIG. 3 comprises a pair of upper and lower circular plates 34,36 sandwiched together to provide a cylindrical space 38 therebetween. This space 38 is divided into eight sectors 40 by radially extending spacers 42. A plurality of wells 44 are provided in each sector 40 (one set of which is shown in broken outline) by forming the upper surface 36a of the lower circular plate 36 as described with reference to FIG. 1. The wells 44 are of the same size and are spaced as for FIG. 1.

Each sector 40 provides a chamber or space 46 which can be filled independently via openings 48 provided through the top surface of each sector 40. The peripheral edge 50 of each sector 40 is open to the surrounding space to provide a vent for the sector 40 to allow liquid to flow through the space or chamber 46 by displacing air therefrom.

In order to enable the disk 32 to be compatible with scanning devices such as are described in WO 96/09548, the upper and/or lower plates 34,36 are made of transparent polycarbonate to enable a liquid beam to be scanned across the disk surface. The disk 32 is provided with a central hole 52 to enable the disk 32 to be mounted on a rotatable shaft.

Figure 7:
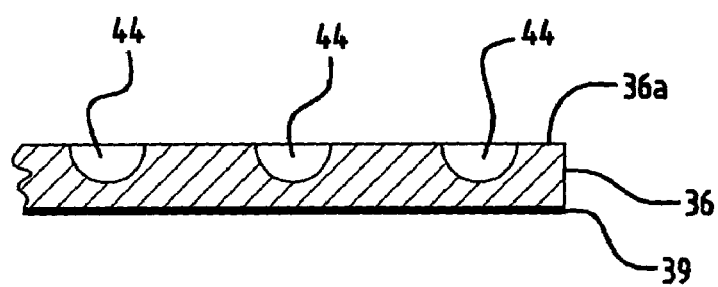
FIG. 7 shows a plate structure including digitally encoded address information.

As is described in W/O96/09548, one of the surfaces of the upper of lower plates 34, 36 may be provided with digitally encoded address information, as indicated at 39 in FIG. 7, which can be read by the scanned light beam. This information may be encoded by way of "pits" and "lans" pressed or moulded into one of the plates. This address information can be used to provide accurate location information on the part of the disk which is being scanned by the light beam.

There is shown in FIG. 4 a third embodiment of a disk assay plate 54 which comprises upper and lower circular transparent polycarbonate plates 56,58 which are spaced apart by a number of radially extending spacer walls 60 to create a plurality of disk sectors 62. The inner surfaces 56a,58a of the circular plates 56,58 are both planar.

Figures 4A, 4B, 4C, 4D:
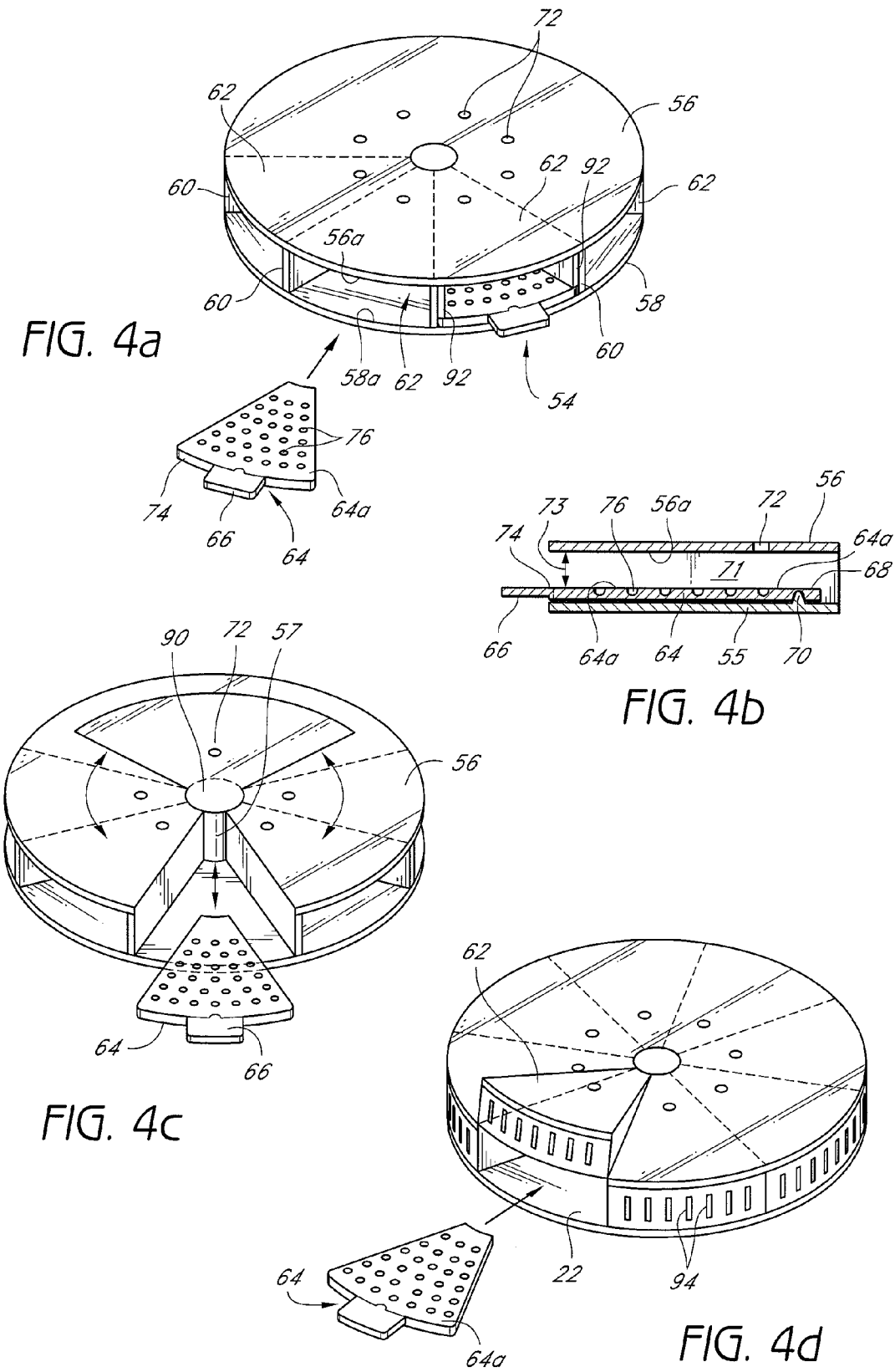
FIG. 4a shows a third embodiment of a disc-style structure for conducting multi-tests.
FIG. 4b shows an enlarged cross-sectional detail of FIG. 4a to allow snap-fitting of the plates in the disc sectors.
FIG. 4c is a fourth embodiment of a disc-style structure for conducting multi-tests.
FIG. 4d shows a modification of the outer disc with hinged sectors and which is applicable to the previous embodiments.

Each disk sector 62 is arranged to receive a sector plate insert 64 which is a transparent polycarbonate plate with a detachable handle 66 on the outer side to facilitate entry and removal of the plate insert 64 in the sector 62. The plate insert 64 and spacer wall 60 have respective recesses/projections (not shown in the interest of clarity) which allow the plate insert 64 to be inserted only in the correct orientation. The plate insert 64 has a groove 68, as shown in FIG. 4b for example, which allows the inset to be snap-fitted over a projection 70 upstanding from plate 58 into the sector. The thickness of the sector plate insert 64 is marginally less than the spacing provided between the upper and lower plates 56, 58 so that the plate insert 64 can be pressed/fitted into one of the disk sector 62 to define a liquid receiving chamber or space 73 between the upper surface 64a of the plate insert 64 and the lower surface 56a of the upper disk plate 56. Openings 72 are provided through the upper disk plate 56 into each disk sector 64 whilst the space 70 between the radially outermost peripheral edge 74 of the insert plate 64 and the upper plate 56 provides a further vent or filling opening into the disk sector 62.

The surface 64a of the insert plate 64 is provided with a plurality of wells 76 as described with respect to FIG. 1. The wells are 2 mm in diameter, 1 mm in depth and 4 mm apart (spaced between centres). These wells are filled by introducing liquid into the disk sector 64 through the upper opening 72 to fill space 70 and subsequently withdrawing the liquid through the same opening as previously described.

Reference is now made to FIG. 5 of the drawings which depicts assay apparatus for conducting an assay on reactions carried out using the assay plate structures of the already described embodiments. However, for convenience, the assay apparatus will be described in combination with the preferred embodiment shown in FIGS. 4a,b with like numerals referring to like parts.

In this case the plate 54 is mounted on a shaft 74 carried by a turntable 77. The apparatus includes a suitable automatic fluid filling/withdrawal system, generally indicated by reference numeral 80, which operates a syringe 82 to dispense/retrieve fluid from a reservoir 84 via the openings 72 into the space 70 between the plate surface 56a and the surface 64a of each sector plate 64. The fluid can of course be dispensed and retained manually if desired. This is achieved for each sector by rotating the disk plate 54 to a suitable position to allow fluid filling/withdrawal. It will be appreciated that the plates are pre-prepared with various reagents, e.g. antigens, and they are inserted in the appropriate wells 76, as described with reference to FIGS. 4a,4b. The plates are first flooded with fluid carrying antibodies and withdrawal of the fluid leaves the antibody/antigen reagents filling the wells 76 resulting in a reaction.

The following example of an assay within the embodiment shown in FIG. 4b is described to provide a better understanding of the steps involved:

Multi-Antigen Elisa Using Sectors

1. The underside of upper surface (56a) of is coated with silicone spray to aid fluid movement. Sector plates 64 are also coated including wells 76. Any excess silicone is removed.
2. Sectors wells 76 are loaded by hand with a panel of seven antigens—Human Serum Albumin, Antitrypsin, Macroglobulin, Antithrombin III, Catalase, Antichymotrypsin and Plasminogen at a concentration of 20 ug/ml in PBS and a volume of 2 ul/well. Control wells contain PBS only. Antigens can be arranged in blocks of the same on the sector plate 64 in a series giving a panel of tests evenly distributed over the sector. Incubate at room temperature for 15 minutes.
3. Wash with 0.05% PBS-Tween using flood/fill technique—1 ml is flooded across the sector plate via holes 72 in the top plate using a 1 ml pipette. This pipetted up and down three times then withdrawn and the washing discarded. This repeated a further three times to ensure complete washing.

4. Blocking is carried out to prevent reactions occurring other than at well sites with 50 mg/ml Bovine Serum Albumin (BSA) (in PBS) using flood/fill. 1 ml of BSA/PBS is flooded across the sector, pipetted up and down three times, withdrawn and discarded. This allows all wells 76 to be filled simultaneously. Incubate for 15 minutes at room temperature.

5. Wash as before.

6. Primary antibodies are applied to the sector plate 64 as a mixture using flood/fill with each individual antibody at the following concentrations: anti-Human Serum Albumin $\frac{1}{1000}$, anti-Antitrypsin $\frac{1}{2000}$, anti-Macroglobulin $\frac{1}{2000}$, anti-Antithrombin III $\frac{1}{1000}$, anti-Catalase 1,1000, anti-Antichymotrypsin $\frac{1}{1000}$, anti-Plasminogen $\frac{1}{1000}$. Antibodies are diluted in 0.5 mg/ml BSA/PBS. Incubate for 10 minutes at room temperature.

7. Wash as before.

8. Second antibody is Amdex anti-IgG (peroxidase conjugate) at a concentration of $\frac{1}{1000}$ in 0.5 mg/ml BSA/PGS. After washing this is applied to the sector using flood/fill. Incubate at room temperature for 10 minutes.

9. Wash as before.

10. The substrate is insoluble Tetramethylbenzidine (TMB). This reacts with the peroxidase on the second antibody to produce an intense blue colour. After washing this is applied to the sector plate 64 by flood/fill but is left flooded across the sector plate 64 after pipetting up and down several times. Incubate for 10 minutes at room temperature.

11. Remove TMB and discard. Wash out the wells with distilled water four times by flood/fill. A blue precipitate will be evident in wells with a positive reaction. No colour is produced in negative wells. Store sections in dark as TMB will slowly fade in daylight. The date for the above assay is shown in FIG. 6a and is graphically represented in FIG. 6b which is reproducible and is representative of a large number of experiments (712).

It will be seen that there is a significant measurable change for each antibody/antigen reaction compared with the background level. The reaction results in an optical change, from transparent to coloured (blue) and which is measured using an optical detector which measures light transmissivity through the disk and wells. In this case optical assessment was carried out using the apparatus as shown in FIG. 5 by locating the plate 64 in a light transmissive microscope 80 (Zeiss Axiophot fitted with a JVC video camera 83 (Model No. TK-1280E)) and sensing the change in optical signal. The output of the video camera is connected to Macintosh IICx 85 with video frame capture. The results can be displayed via the MAC display 87 or a hard copy provided by printer 86. Analysis was carried out by measuring means grayscale values in centre of wells quantified by NIH Image software. Background levels taken from sectors which had not been exposed to immuno-chemicals or chromogen were subtracted from all experimental wells. Experimental wells contained array or seven separate antigens listed above. In addition, experimental controls were carried out in which specific antigen was omitted wells and wells exposed to the same regime of blocking, antibody binding and exposure to chromogenis substrate. The average reading from these experimental controls minus mean reading from the sector alone was defined as the background level of straining. Experimental readings from the seven specific antigens providing signals of approximately five to six times greater than this background. It will be observed that there is no cross-contamination between wells 76 become of the efficiency of withdrawal and because the substrate in this case is insoluble. However, this assay would also work satisfactorily for soluble substrates because of fluid withdrawal from the sector plate 64 leaving fluid in the wells 76 only, not on surface 64a.

In a modification, if it was unnecessary to withdraw all of the liquid to leave a film on surface 64, the assay would still work with an insoluble substrate in each well, cross-contamination would still not occur. However, this arrangement would be unsatisfactory for soluble substrates in the wells as the film could cause dispersal to other locations and provide contamination of other wells.

With the embodiment shown in FIGS. 4a,4b the disk sector plate 54 is more suitable for conducting a variety of different assays, e.g. antigen/antibody assays for different patients, i.e. one patient/sector.

Figure 8:
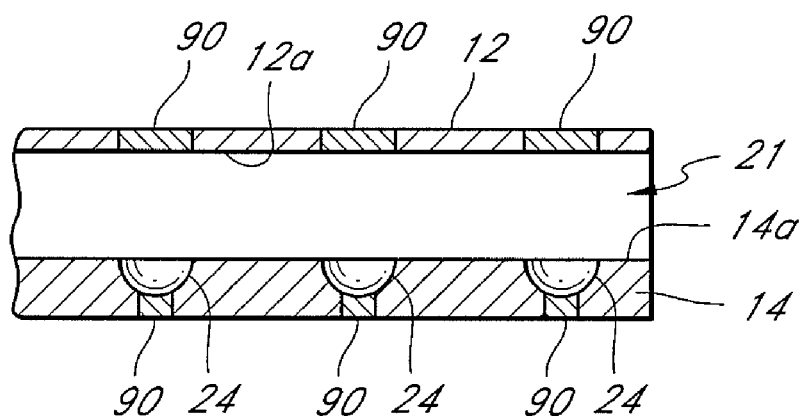
FIG. 8 corresponds to FIG. 2d with the location of lenses 90 shown.

It will be appreciated that modification may be made to the above described embodiments without departing from the scope of the present invention. For example, the opening through which a liquid analyte is introduced may be provided through the lower plate of the multi-well container. More than one opening can be used for faster flooding. This opening may be arranged to receive the tip of a syringe needle. The vent opening may also be provided in any one of the walls of the container although it is preferably provided in a peripheral wall. The opening 22 may be provided by a single opening 22 or by a series of openings or vents as shown in FIG. 4d for example. A laser may be used with CD optics instead of the microscope and video camera for the embodiment of FIG. 4. The top plate in the embodiment of FIGS. 3 and 4 may be snap-fitted to the lower plate and may be snap-fitted onto a CD base plate which would receive sections and provide the advantage of positioned information. As shown in FIG. 4c the upper plant surface 56 can have sector covers connected to a lower surface or central boss by a hinge, for example integrated living hinge 90 at the inner radius to allow each disk sector 62 to be pivotally raised and lowered and allow sector plates 64 to be inserted into each sector. The well size and spacing may be varied as required, for example the wells could be 3 mm in diameter; 1.5 mm apart and spaced 5.5 mm between centre. The exact size and spacing is a matter of choice consistent with the requirement that fluid is retained in the wells after withdrawal as described above. However, the wells could also be filled during flooding of the space depending on the well size, type of plastic and fluid properties. However, liquid will still be retained in the wells upon withdrawal of the liquid. Also, the structure and inserts made may be of any suitable optical transmissive plastic, such as polystyrene or perspex™. The handle 66 may be integrated with or detachable from plate 64. As shown in FIG. 4a the radially extending ribs may have radial shoulders 92 to define a recess 94 for receiving the plate 64 also defining the spacing height between the surface 64a of the plate 64 and the underside 56a for receiving the liquid. Suitable materials may be used to coat the interior of the sectors to aid fluid movement as described with reference to silicone above. This may be applied to the underside of the top surface and to the top surface of the plats as for the other embodiments. Suitable materials may be used to increase the hydrophobicity of liquid across the sector and hydrophilicity to the movement of liquid into the desired location, e.g. wells. The wells may be coated by a suitable optical reflective material to enhance the reflection of light and observation of reactions occurring within the wells and, similarly, lenses 90 may be located in the top or bottom light transmissive plates 12 and 14 as seen in FIG. 8, to improve optical assessment of the reaction. These lenses may be mounded into the upper or lower plates of the exemplary embodiments during the manufacture as is well known in plastic moulding processes. Separate optical elements may be used instead, if appropriate.

In a modification to the embodiments described, the wells are absent from the upper surface of the plate and that plate retains its planar surface to enable a thin, uniform layer of liquid to be introduced into the space between the upper disk plate and the insert plate. An insoluble substrate with reagent or reagents (e.g. an antigen) may be applied directly to the planar surface of the insert plate by for example applying spots of reagent thereto.

For certain applications, it may be appropriate to provide each insert with a lid which can be slid into the space between the insert and the upper plate 22 of the disk following filling of the wells. The lower surface of the lid may be arrange to be flush with the surface of the insert so as to close off each well. This prevents liquid from being thrown out of the wells during spinning of the disk during automated reading and analysis. The invention has use in immunoassay applications including tests for sexually transmitted diseases, parasites, allergens, cancer markers and cardiac markers, either in laboratories or at point-of-care locations, for example medical practitioners offices or the like. Other applications of the invention are in chemical and biochemical assays. Examples of such assays include immunoassay, clinical biochemistry tests, nucleic acid analysis and receptor ligand interactions. Examples of clinical biochemistry uses would be in measurement of serum analytes such as glucose, urea, creatinine and enzymes such as alkaline phosphatase. Immunoassay application include tests designed to detect infections organisms, viruses, parasites as well as endogenous analytes such as circulating hormone levels and cancer markers. Examples of chemical analysis include measure of phosphate and nitrate levels in water, environmental and industrial monitoring including potable and waste water and process monitoring. The system could be used in a variety of settings including clinical laboratories, doctor's and veterinary surgeries as well as industrial and research laboratories.

The invention claimed is:

1. A multi-reaction site assay plate structure comprising:
   an upper substantially planar, rigid surface;
   a lower closely spaced opposed and substantially planar, rigid surface
   a plurality of dividers extending between said upper and lower surfaces so as to define a space therebetween, and to define a plurality of sectors that are configured to receive a sector plate insert;
   at least one coverless sector plate insert configured to be removeably inserted in a sector so as to define a liquid receiving chamber between the upper surface of the sector plate insert and the upper rigid surface, wherein said upper surface of the sector plate insert comprises a plurality of separate reaction sites;
   at least one first opening in one of said upper and lower surfaces providing access to said chamber for introduction of fluid thereto from an external location, the sites being such that when excess fluid is subsequently withdrawn through said at least one first opening some of said fluid is left at said sites; and
   encoded information stored in at least one of said upper and lower surfaces so as to be readable by a scanned light beam, said encoded information including address information providing location information as to the part of said assay plate structure being scanned by the light beam.

2. The assay plate structure of claim 1 wherein the spacing between said upper and lower surfaces is sufficiently small to facilitate the flow in said chamber by capillary action to substantially fill the space and cover all of the sites.

3. The assay plate structure of claim 1 wherein the spacing is less than 1 mm.

4. The assay plate structure of claim 2 wherein said at least one first opening is configured to received the end of a liquid injecting device, and said at least one first opening forms a substantially air-tightly seal around said end.

5. The assay plate structure of claim 1 wherein the multi-reaction site structure is a disc which includes upper and lower circuit plates, the internal surfaces of which respectively define said upper lower opposed surfaces.

6. The assay plate structure of claim 5 further comprising at least one second opening located at the peripheral edge of the disc.

7. The assay plate structure of claim 6 wherein sector is provided with at least one of said first openings and at least one of said second openings to enable each sector to be independently filled.

8. The assay plate structure of claim 5 wherein at least one of the upper and lower plates forming the structure are transparent to enable optical inspection of the sites from outside the structure.

9. The assay plate structure of claim 8 wherein the other of the upper and lower includes a reflecting surface for providing improved signal detection.

10. The assay plate structure of claim 1 wherein the plate structure is provided in the form of a disc and said enclosed information is digitally encoded.

11. The assay plate structure of claim 10 wherein at least a portion of the plate structure is transparent for optical inspection of said reaction sites.

12. The assay plate structure of claim 1, wherein the reaction sites comprise wells configured to receive a portion of said fluid.

13. The assay plate structure of claim 1 wherein the upper rigid surface includes at least one moveable portions corresponding with an adjacent sector, wherein the moveable portion is configured to move with respect to the remainder of the upper rigid surface so as to permit insertion and removal of the sector plate insert into and out of said adjacent sector.

14. An optionally transparent structure for conducting assays said structure comprising:
   one or more chambers, each having an upper substantially planar, rigid surface and a lower closely spaced opposed and substantially planar, rigid surface, said upper and lower surfaces separated by a plurality of dividers extending therebetween so as to define a space therebetween and to define a plurality of sectors that are configured to receive a sector plate insert, at least one of said upper and lower surfaces having at least one first opening for introduction of fluid therethrough into said one or more chambers;
   at least one coverless sector plate insert positioned within one of the sectors; and
   encoded information stored in at least one of said upper and lower surfaces so as to be readable by a scanned light beam, said encoded information including address information providing location information as to the part of said structure being scanned by the light beam for at least one of a plurality of surface locations on the at least one insert.

15. The structure of claim 14 wherein areas between said surface locations include hydrophobic coatings.

16. The structure of claim 14 wherein said surfaces are provided by respective upper and lower plates of a disc.

17. The structure of claim 16 wherein said encoded address information is provided for optical inspection of said at least one of said plurality of surface locations from exteriorly of said structure.

18. The structure of claim 14 wherein said at least one first opening is configured to receive the end of a liquid injecting device, and said at least one first opening forms a substantially air-tight seal around said end.

19. The structure of claim 14 wherein the structure is a disc which includes upper and lower circular plates, the internal surfaces of which respectively define said upper and lower opposed surfaces.

20. The structure of claim 19 further comprising at least one second opening located at a peripheral edge of the disc to vent said space.

21. The structure of claim 20 wherein sector is provided with at least one of said first openings and at least one of said second openings to enable independent access to each sector.

22. The structure of claim 21 wherein the dividers are radially extending.

23. The structure of claim 19 wherein at least one of the upper and lower plates forming the structure is transparent to enable optical inspection of the surface locations from outside the structure, and the outer of the upper and lower plates includes a reflecting surface.

24. The structure of claim 19 wherein the structure is made of plastic and said at least one insert is snap-fitted onto the disc.

25. The structure of claim 24 wherein the disc and the at least one insert include lock and key portions to allow the at least one insert.

26. The structure of claim 14 including one or more lenses to improve the optical inspection of said surface locations.

27. The structure of claim 26 wherein said one or more lenses are molded into said structure.

28. The structure of claim 14, wherein the surface locations bear a hydrophilic coating and comprise wells configured to receive a portion of said fluid.

29. The assay plate structure of claim 14 wherein the upper rigid surface includes at least one movable portion corresponding with an adjacent sector, wherein the moveable portion is configured to move with respect to the remainder of the upper rigid surface so as to permit insertion and removed of the sector plate insert into and out of said adjacent sector.

30. A multi-reaction site assay plate structure comprising:
an upper substantially planar, rigid surface and a lower closely spaced opposed and substantially planar, rigid surface, said upper and lower surfaces separated by a plurality of dividers extending therebetween so as to define a space therebetween and to define a plurality of sectors that are configured to receive a sector plate insert, and at least one of said upper and lower surfaces having at least one first opening for the introduction of a fluid therethrough into said space;
at least one covered sector plate insert positioned within one of the sectors, the insert having a plurality of separate reaction sites; and
encoded information stored in at least one of said upper and lower surfaces so as to be readable by a scanned light beam, said encoded information including address information providing location information as to the part of the assay plate structure being scanned by the light beam.

31. The assay plate structure of claim 30 wherein said at least one first opening is configured to receive the end of a liquid injecting device, and said at least one first opening forms a substantially air-tight seal around said end.

32. The assay plate structure of claim 30 wherein the structure is an optically transparent disc which includes upper and lower circular plates, the internal surfaces of which respectively define said upper and lower opposed surfaces.

33. The assay plate structure of claim 32 further comprising at least one second opening located at a peripheral edge of the disc.

34. The assay plate structure of claim 33 wherein ecah sector is provided with at least one of said first openings and at least one of said second openings to enable each sector to be independently accessed.

35. The assay plate structure of claim 32 wherein at least one of the upper and lower plates forming the structure are transparent to enable optical inspection of the sites from outside the structure.

36. The assay plate structure of claim 35 wherein the other of the upper and lower plates includes a reflecting surface.

37. The assay plate structure of claim 32 wherein said encoded address information is digitally encoded.

38. The assay plate structure of claim 30, wherein the reaction sites comprise wells configured to receive a portion of said fluid.

39. The assay plate structure of claim 30 wherein the upper rigid surface includes at least one moveable portion corresponding with an adjacent sector, wherein the moveable portion is configured to move with respect to the remainder of the upper rigid surface so as to permit insertion and removal of the sector plate insert into and out of said adjacent sector.

* * * * *